United States Patent [19]

Cohen

[11] Patent Number: 5,649,913
[45] Date of Patent: Jul. 22, 1997

[54] MEN'S BOXER SHORTS FOR INCONTINENCE

[76] Inventor: Morton H. Cohen, 207 McMillen Ave., Beaver Falls, Pa. 15010

[21] Appl. No.: 465,531

[22] Filed: Jun. 5, 1995

[51] Int. Cl.⁶ ............... A61F 5/44; A61B 9/00
[52] U.S. Cl. ...................... 604/353; 2/401
[58] Field of Search .......... 2/401, 403; 604/329, 604/349, 353

[56] References Cited

U.S. PATENT DOCUMENTS 3,547,123  12/1970  Sachs ........................... 604/353
4,601,716  7/1986  Smith ........................... 604/353
4,955,088  9/1990  Terjesen ....................... 2/403
5,342,332  8/1994  Wheeler ........................ 604/349

FOREIGN PATENT DOCUMENTS 06271177  12/1994  European Pat. Off. ........ 2/403

Primary Examiner—Robert A. Clarke
Attorney, Agent, or Firm—Carothers & Carothers

[57] ABSTRACT

Men's boxer shorts for incontinence. The front panel thereof has a bottom which is turned upwardly to form a pocket for receiving and storing urine. A ring, of elastic or soft cloth material, is attached to the top of the pocket for encircling a man's penis to direct the flow of urine into the pocket.

3 Claims, 1 Drawing Sheet

MEN'S BOXER SHORTS FOR INCONTINENCE

BACKGROUND OF THE INVENTION

Present men's boxer shorts for controlling incontinence have absorbent portions but do not control the direction of urinal flow and storage and absorbtion of urine.

SUMMARY OF THE INVENTION

Men's boxer shorts constructed to control the direction and storage of urine.

DESCRIPTION OF THE PREFERRED EMBODIMENT

Figure 1:
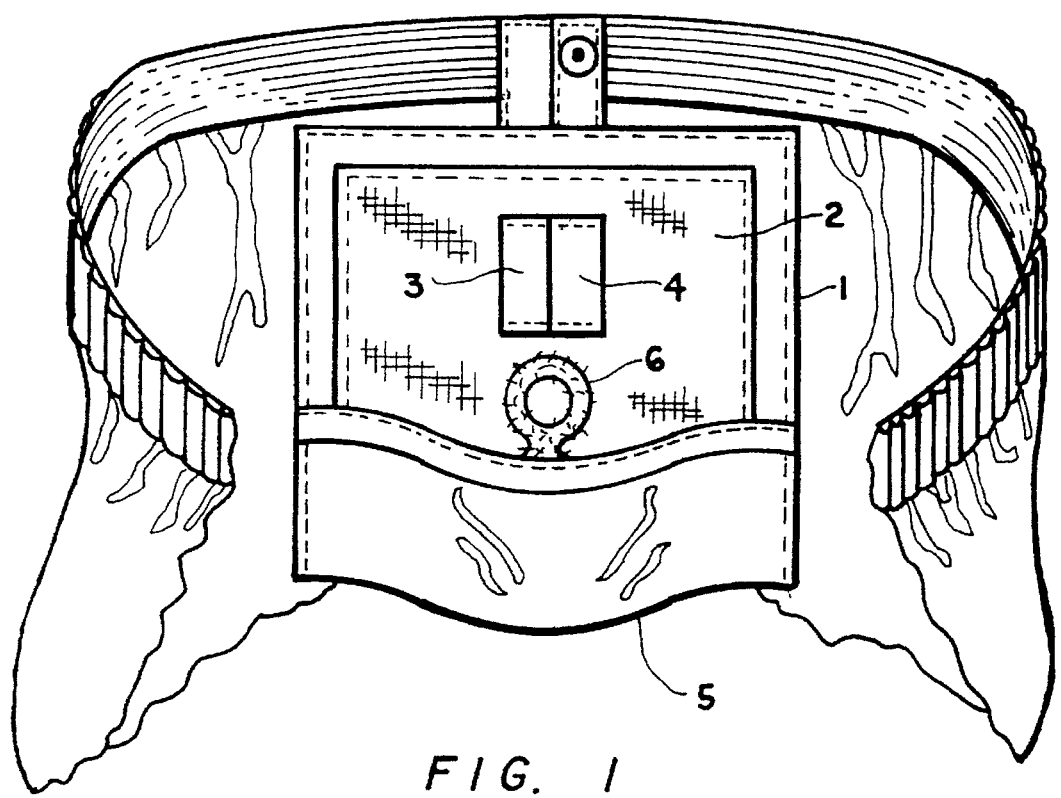
FIG. 1 shows an inside view of men's boxer shorts embodying the present invention.

FIG. 1 shows the inside view of the front panel of men's boxer shorts constructed for incontinents, showing the direction of flow, as well as storage, and absorbtion of urine.

Numeral 1 denotes a panel of waterproof material, such as nylon, over which is attached a panel of perforated material 2, to provide comfort, having an openable fly opening comprising overlapping panels 3 and 4 of water proof material.

The bottom of panel 2 is turned upwardly at 5 to form a pocket for receiving, storing and absorbing urine. Attached to top of said pocket is an elastic ring 6 for attachment around the man's penis to provide closeness to the body and so as to direct his flow of urine into said pocket. Ring 6 in some cases need not be of elastic material but merely soft cloth, or the like.

In operation, as urine is discharged from a man's penis, it is directed into pocket 5 wherein it is stored without wetting discomfort to the man. Therefore, the urine does not provide discomfort to the man's body.

I claim:

1. A combination of a boxer shorts and a channel shaped attachment for controlling incontinence comprising:
   a) a front portion in the boxer shorts,
   b) a fly opening in the front portion,
   c) wherein the channel shaped attachment is secured to the inside of the front portion for receiving urine,
   d) wherein the channel shaped attachment has a free portion unsecured to the front portion of the boxer shorts and,
   e) a ring attached to the top of the free portion of the attachment for encircling a man's penis and directing urinal flow into said channel shaped attachment.

2. The combination recited in claim 1 wherein said ring is of elastic material.

3. The combination recited in claim 1 wherein said ring is of soft cloth material.

* * * * *